(12) United States Patent
Langen

(10) Patent No.: US 8,541,549 B2
(45) Date of Patent: Sep. 24, 2013

(54) ANNEXIN-BASED APOPTOSIS MARKERS

(75) Inventor: Ralf Langen, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 743 days.

(21) Appl. No.: 12/416,772

(22) Filed: Apr. 1, 2009

(65) Prior Publication Data

US 2009/0246802 A1  Oct. 1, 2009

Related U.S. Application Data

(60) Provisional application No. 61/041,550, filed on Apr. 1, 2008.

(51) Int. Cl.
*C12P 17/06* (2006.01)
*C07K 1/13* (2006.01)
*A61K 38/00* (2006.01)

(52) U.S. Cl.
USPC ........... 530/350; 530/39.1; 530/300; 514/1.1; 362/614; 362/217.08; 362/260

(58) Field of Classification Search
None
See application file for complete search history.

(56) References Cited

U.S. PATENT DOCUMENTS

| | | | |
|---|---|---|---|
| 6,521,446 B2 | 2/2003 | Hellinga | |
| 2002/0142347 A1 | 10/2002 | Knudsen et al. | |
| 2002/0146730 A1* | 10/2002 | Liu et al. ........................... | 435/6 |
| 2004/0022731 A1* | 2/2004 | Bogdanov et al. ............. | 424/9.6 |
| 2006/0009381 A1 | 1/2006 | Reutelingsperger | |

OTHER PUBLICATIONS

Rescher et al. (2004) Annexins—unique membrane binding proteins with diverse functions, J. Cell Sci., vol. 117, pp. 2631-2639.*
Wikipedia (2011, updated) Annexin, en.wikipedia.org/wiki/Annexin, pp. 1-10.*
Ladokhin et al. (2002) Determining the Membrane Topology of Proteins: Insertion Pathway of a Transmembrane Helix of Annexin 12, Biochemistry, vol. 41, pp. 13617-13626.*
Langen et al. (1998) A transmembrane form of annexin XII detected by site-directed spin labeling, Proc. Natl. Acad. Sci. U S A., vol. 95, No. 24, pp. 12060-14065.*
Tait et al. (2006) Improved detection of cell death in vivo with annexin V radiolabeled by site-specific methods, J. Nucl. Med., vol. 47, No. 9, pp. 15461553.*
Patel et al. (20050 The conserved core domains of annexins A1, A2, A5, and B12 can be divided into two groups with different Ca2+-dependent membrane-binding properties, Biochemistry, vol. 44, No. 8, pp. 2833-2844.*
Hoekstra et al. (1993) Interaction of Annexins with Membranes: The N-Terminus as a Governing Parameter as Revealed with a Chimeric Annexin, Biochemistry, vol., 31, pp. 14194-14202.*
Posokhov et al. (Apr. 12, 2008) "Membrane Insertion Pathway of Annexin B12: Thermodynamic and Kinetic Characterization by Fluorescence Correlation Spectroscopy and Fluorescence Quenching" Biochemistry, vol. 47, No. 18, pp. 5078-5087.*
Winter et al. (2006) Biochemical characterization of annexin B1 from Cysticercus cellulosae, FEBS J., vol. 273, No. 14, pp. 3238-3247.*
Luecke et al. (1995) Crystal structure of the annexin XII hexamer and implications for bilayer insertion, Nature, vol. 378, pp. 512-515.*
Schlaepfer et al. (1992) Identification of a novel annexin in Hydra vulgaris. Characterization, cDNA cloning, and protein kinase C phosphorylation of annexin XII, J. Biol. Chem., vol. 267, No. 14, pp. 9529-9539.*
Fischer et al. (Mar. 2007) Annexin B12 Is a Sensor of Membrane Curvature and Undergoes Major Curvature-dependent Structural Changes, J. Biol. Chem., vol. 282, No. 13, pp. 9996-10004.*

\* cited by examiner

*Primary Examiner* — Manjunath Rao
*Assistant Examiner* — Samuel Liu
(74) *Attorney, Agent, or Firm* — Seth D. Levy; Nixon Peabody LLP

(57) ABSTRACT

The present invention describes an annexin derivative and a method of using the annexin derivative as a biosensor for real-time visualization of phosphatidylserine exposure, apoptosis, live-cell imaging and monitoring of cell health.

17 Claims, 7 Drawing Sheets
(4 of 7 Drawing Sheet(s) Filed in Color)

FIG. 7

```
1    MVVGTVKPHASFN  14
15   SREDAFTLRKAMKGLGTDEKSITHILATRSNAQRQQIKTDYTTLFGKHLEDELKSELSGNYEAAALALLRK  85
86   EDEELAEQLHAAMKGLGTDENALIDILCTQSNAQIHAIKAAFKLLYKEDLEKEIISETSGNFQRLLVSMLQGGRKEDEPVN  166
167  AAHAARDAAAIYQAGEGQIGTDESRFMAVLATRSYPQLHQIPHEYSFISNKTILQAIENEFSGDIKNGLLAIVKSVE  243
244  NREAYFABRLRHAAMKGLGTSDKTLIRILVSRSEIDLANIKETPQAMYGKSLYEFIADDCSGDYKDLLLQITGH  316
```

ANNEXIN-BASED APOPTOSIS MARKERS

This application claims benefit of priority to U.S. Provisional Application Ser. No. 61/041,550, filed Apr. 1, 2008, and is incorporated herein by reference in its entirety.

FIELD OF INVENTION

This invention relates to annexin derivatives and the detection of a cell that exposes phosphatidylserine on its extracellular membrane leaflet; for example, an apoptotic cell.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Live-cell imaging has become a valuable technique for studying dynamic biological processes in real-time. The ability to visualize and track active processes in a single living cell has provided new insights into cellular architecture, membrane organization, dynamic protein assemblies, molecular organization, and cellular responses to external signals.

Central to these types of experiments is the knowledge of the general health of the culture and the cell of interest. While the morphological and biochemical changes that occur at different stages of apoptosis are well understood, unambiguously imaging these changes in living cells has been difficult. Several assays are available, which are aimed at detecting the specific biochemical changes that occur at the different stages of apoptosis, such as, phosphatidylserine exposure to the outer leaflet of the plasma membrane, mitochondrial dysfunction, activation of caspases, DNA fragmentation, and loss of membrane integrity. However, the current methods for these assays are generally disruptive to the cellular environment and, in most cases, are toxic to the cells.

A number of reasons make the detection of phosphatidylserine translocation to the extracellular face of the plasma membrane an attractive target for live-cell imaging. In healthy cells, plasma membrane asymmetry is closely regulated, and phosphatidylserine is restricted to the inner leaflet. Exposure of phosphatidylserine has been well established as a near universal indicator of apoptosis. In addition, phosphatidylserine provides abundant and easily accessible binding targets that can be detected without the need to penetrate into the cell. Moreover, it is an early event, thus monitoring phosphatidylserine exposure provides a way to observe the initiation of the apoptotic pathway before other changes are present. This is particularly useful for the detection of apoptotic processes in which progression into cell death does not occur; for example, in neuronal pruning or developmental axonal degeneration.

Annexins represent a highly conserved family of proteins that selectively bind to negatively charged, phosphatidylserine containing phospholipid membranes in the presence of calcium ions ($Ca^{2+}$). Dying cells undergoing apoptosis expose these negatively charged lipids on the outer leaflet of the plasma membrane. Therefore, annexins selectively bind to apoptotic cells. This diagnostic application of annexins was first demonstrated using fluorescently labeled annexin A5 (Vermes et al. *A novel assay for apoptosis. Flow cytometric detection of phosphatidylserine expression on early apoptotic cells using fluorescein labeled Annexin V*. (1995) J. IMMUNOL. METH. 184:39-51). The originally described annexin A5-based assay has been widely used in biological applications and has not been modified significantly. Modifications to the annexin A5-based assay have been limited to the use of different fluorophores that allow detection of fluorescent signals of different colors.

However, annexin-based probes described to date are impractical for live-cell imaging experiments since separate steps are required for binding of the fluorescent annexin probe to the apoptotic cells and subsequent removal of the unbound protein in order to reduce the background before analysis by fluorescence microscopy. Not only is the washing step an additional step, it places a limitation on real-time imaging of apoptotic cells and high-throughput screening for apoptotic cells. Thus, there exists a need in the art for a simpler apoptosis detection method, real-time and high-throughput apoptosis detection, as well as monitoring cell health.

SUMMARY OF THE INVENTION

The following embodiments and aspects thereof are described and illustrated in conjunction with compositions and methods which are meant to be exemplary and illustrative, not limiting in scope.

The present invention provides for an annexin derivative, comprising: an annexin comprising one or more amino acids conjugated to a polarity sensitive fluorophore, wherein the one or more amino acids were inserted into or substituted at a polarity changing site on the annexin.

In one embodiment, the annexin may be a cysteine less or lysine less variant prior to the insertion or substitution of the one or more amino acids at the polarity changing site, or a cysteine or lysine may be deleted or substituted away from a wild-type annexin during the insertion or substitution of the one or more amino acids at the polarity changing site.

In one embodiment, the polarity changing site on the annexin may be a membrane-interaction site on the annexin or a site that undergoes a conformational change. In a particular embodiment, the polarity changing site may be a loop region on the annexin.

In various embodiments, the annexin may be selected from the group consisting of annexins A1, A2, A3, A4, A5, A6, A7, A8, A9, A10, A11, A13, ci0100146873, ci0100136930, ci0100137443, ci0100153687, and ci0100138049, B9, B10, B11, B13, nex-1, nex-2, nex-3, nex-4, C1, C2, D1, D2, D3, D4, D5, D6, D7, D8, D9, D10, D11, D12, D13, D14, D15, D16, D17, D18, D19, D20, annexins from *Schistosoma mansoni*, and annexins from *Giardia lamblia*.

In one particular embodiment, the annexin may be annexin B12. In this embodiment, the one or more amino acids may be inserted next to or substituted at or around residues 26-33, 70-73, 97-105, 141-145, 180-189, 226-229, 256-264, and/or 301-304; particularly, position 101, 260 or both.

In another particular embodiment, the annexin may be annexin A5. In one embodiment, the one or more amino acids may be inserted next to or substituted at or around a residue at position 262.

In various embodiments, the one or more amino acids that were inserted or substituted into the annexin may be cysteine or lysine.

In various embodiments, the polarity sensitive fluorophore may be N,N'-Dimethyl-N-(iodoacetyl)-N'(7-nitrobenz-2- oxa-1,2-diazol-4-yl)ethylenediamine ("IANBD"), 6-Bromoacetyl-2-dimethylaminonaphthalene ("BADAN"), prodan or dansyl.

The present invention also provides for a kit to detect phosphatidylserine exposure, comprising an annexin derivative of the present invention; and instructions for using the annexin derivative to detect phosphatidylserine exposure. In one embodiment, the annexin derivative provided in the kit may be contained in a cell culture medium.

The present invention also provide for a method of detecting apoptosis, comprising: providing an annexin derivative of the present invention; contacting the annexin derivative to a sample comprising cells; and detecting a fluorescence in the sample.

In one embodiment, detecting the fluorescence comprises detecting an increase of fluorescence intensity; particularly, detecting an increase of one or more orders of magnitude in the intensity; and/or detecting a shift in the wavelength of the fluorescence.

In an embodiment wherein the polarity sensitive fluorophore is IANBD, the fluorescence may be detected at a $\lambda_{max}$ of about 500 to about 600 nm. In an embodiment wherein the polarity sensitive fluorophore is BADAN, the fluorescence may be detected in the blue light range.

In various embodiment, detecting the fluorescence may be performed in real time and/or performed in a high-throughput screening system.

The present invention also describes a method of monitoring cell health, comprising: providing an annexin derivative of the present invention; contacting the annexin derivative to a sample comprising cells; and monitoring the fluorescence, wherein an increase in the fluorescence intensity (particularly, an increase of fluorescence intensity by one or more orders of magnitude) and/or a shift in the wavelength of the fluorescence indicate that a cell is undergoing apoptosis, and an absence of an increase in the fluorescence intensity and/or an absence of a shift in the wavelength of the fluorescence indicate that a cell is healthy.

In another embodiment, the method further comprises administering a therapeutic drug upon detection of one or more cells undergoing apoptosis.

In various embodiments, detecting may be performed in real time and/or in a high-throughput screening system.

The present invention also provides for a membrane-binding protein derivative, comprising: a membrane-binding protein comprising one or more amino acids conjugated to a polarity sensitive fluorophore, wherein the one or more amino acids were inserted into or substituted at a polarity changing site on the protein.

In one embodiment, the membrane-binding protein is a protein that specifically binds to a phosphatidylserine-containing membrane ("phosphatidylserine binding protein"). In a particular embodiment, the phosphatidylserine binding protein may be a C2 domain containing protein.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

The file of this patent contains at least one drawing executed in color. Copies of this patent with color drawing(s) will be provided by the patent and Trademark Office upon request and payment of the necessary fee.

Exemplary embodiments are illustrated in referenced figures. It is intended that the embodiments and figures disclosed herein are to be considered illustrative rather than restrictive.

FIG. 7 depicts the sequence of annexin B12 (SEQ ID NO:1; prior art) showing the location of the loop regions in accordance with an embodiment of the present invention. The cylinders denote the presence of α-helical regions (A-E in domains I-IV) in the crystal structure. The loop residues are those in between helices A and B and Helices D and E (i.e., residues 26-33, 70-73, 97-105, 141-145, 180-189, 226-229, 256-264, and 301-304).

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, N.Y. 2001); March, *Advanced Organic Chemistry Reactions, Mechanisms and Structure* 5th ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

"Annexin derivative" as used herein refers to an annexin in which one or more amino acids have been substituted with another amino acid (e.g., cysteine, lysine) and labeled with a fluorophore, or an annexin in which one or more amino acids (e.g., cysteine, lysine) have been inserted and labeled with a fluorophore.

Figure 2:
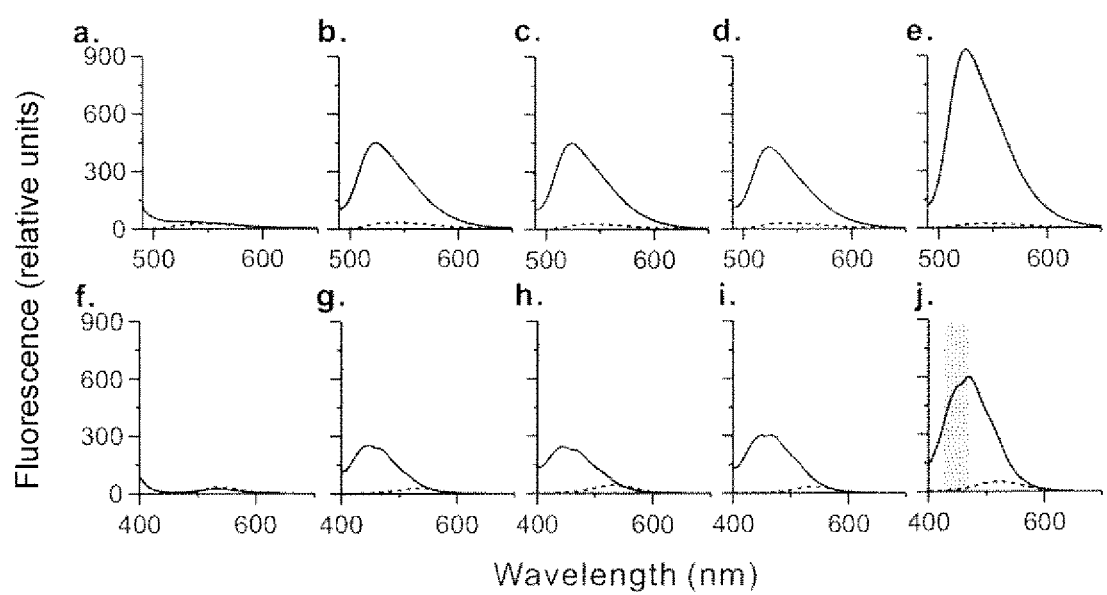
FIG. 2 depicts a comparison of the intensities of the fluorescence between the solution and membrane bound state in accordance with an embodiment of the present invention. Top panel: the excitation wavelength was set to 478 nm and fluorescence emission intensities were measured for IANBD labeled annexins in the solution state (dashed lines) and the membrane-bound state (black lines): a) AnxB12 4C-IANBD, b) AnxB12 101C-IANBD, c) AnxB12 260C-IANBD, d) AnxA5 262C-IANBD and e) AnxB12 101C-, 260C-IANBD (the emission profile of a typical filter set for green fluorescence is shown by the shaded column). Bottom panel: the excitation wavelength was set to 380 nm and the fluorescence emission intensities were measured for BADAN labeled annexins in the solution state (dashed lines) and the membrane-bound state (black lines): f) AnxB12 4C-BADAN, g) AnxB12 101C-BADAN, h) AnxB12 260C-BADAN, i) AnxA5 262C-BADAN and j) AnxB12 101C-, 260C-BADAN (the shaded column denotes the ideal emission profile, 420-470 nm, which may be used for the design of custom filters).

The present invention is based on the inventor's work and on annexins' ability to bind to phosphatidylserine exposing cells; e.g., apoptotic cells. However, it uses a vastly improved and specifically designed detection readout. Previously, annexin A5 had been labeled at the N-terminus with various fluorescent markers. Thus, the fluorescent signal is present regardless of whether the annexin is bound or free. As can be seen in FIG. 2, when a fluorophore is merely labeled at the N-terminus, it does not give a signal change. Detection of apoptotic cells requires incubation of fluorescently tagged annexin followed by washing to remove unbound annexin prior to visualizing the fluorescently labeled cells. This washing step places a limitation on real-time imaging of apoptotic cells and high-throughput screening/diagnosis for apoptotic cells. To overcome these limitations, the inventor developed the annexin derivatives of the present invention, which give rise to a specific signal only when bound to apoptotic or other phosphatidylserine exposing cells. Healthy non-apoptotic cells do not bind annexin and thus, do not give rise to the specific signal.

The present invention describes the design and application of a polarity sensitive annexin-based biosensor (PS-anx) applicable to real-time imaging of apoptotic processes in living cells. It has been well established that membrane interaction of annexin B12 requires the presence of negatively charged phosphatidylserine as well as low micromolar to millimolar concentrations of $Ca^{2+}$. Based on the inventor's previous structural studies of Annexin B12 (AnxB12) in the solution and $Ca^{2+}$-dependent membrane-bound state, the inventor designed PS-anx so that the structural changes which accompany membrane-binding were directly coupled to an "on/off" fluorescence switch. This was accomplished by labeling the specific residues that transition from a polar solution to a non-polar (lipid exposed) environment upon membrane-binding with polarity sensitive fluorophores, IANBD (green fluorescent) and BADAN (blue fluorescent).

To prevent background signal from unbound protein, fluorophores were introduced in specific loop sites located on the membrane interaction surface of annexin B12. In solution, these sites are in an aqueous (i.e., polar) environment, but upon membrane interaction, these sites penetrate into the hydrophobic (i.e., non-polar) membrane environment. By choosing a polarity sensitive fluorophore, it is possible to significantly alter the fluorescence properties. The inventor has successfully tested this approach for two different annexin B12 derivatives, which were labeled with two different fluorophores, 6-Bromoacetyl-2-dimethylaminonaphthalene ("BADAN") and N,N'-Dimethyl-N-(iodoacetyl)-N'(7-nitrobenz-2-oxa-1,2-diazol-4-yl)ethylenediamine ("IANBD" or "NBD") (see FIG. 2). Based upon the successful results, the inventor further applied the technology to annexin A5 and also achieved successful results. Based upon the clear results and because annexins are found to be highly homologous, the same approach can be applied to other members of the annexin family of proteins as well as any other phosphatidylserine binding proteins.

Figure 6:
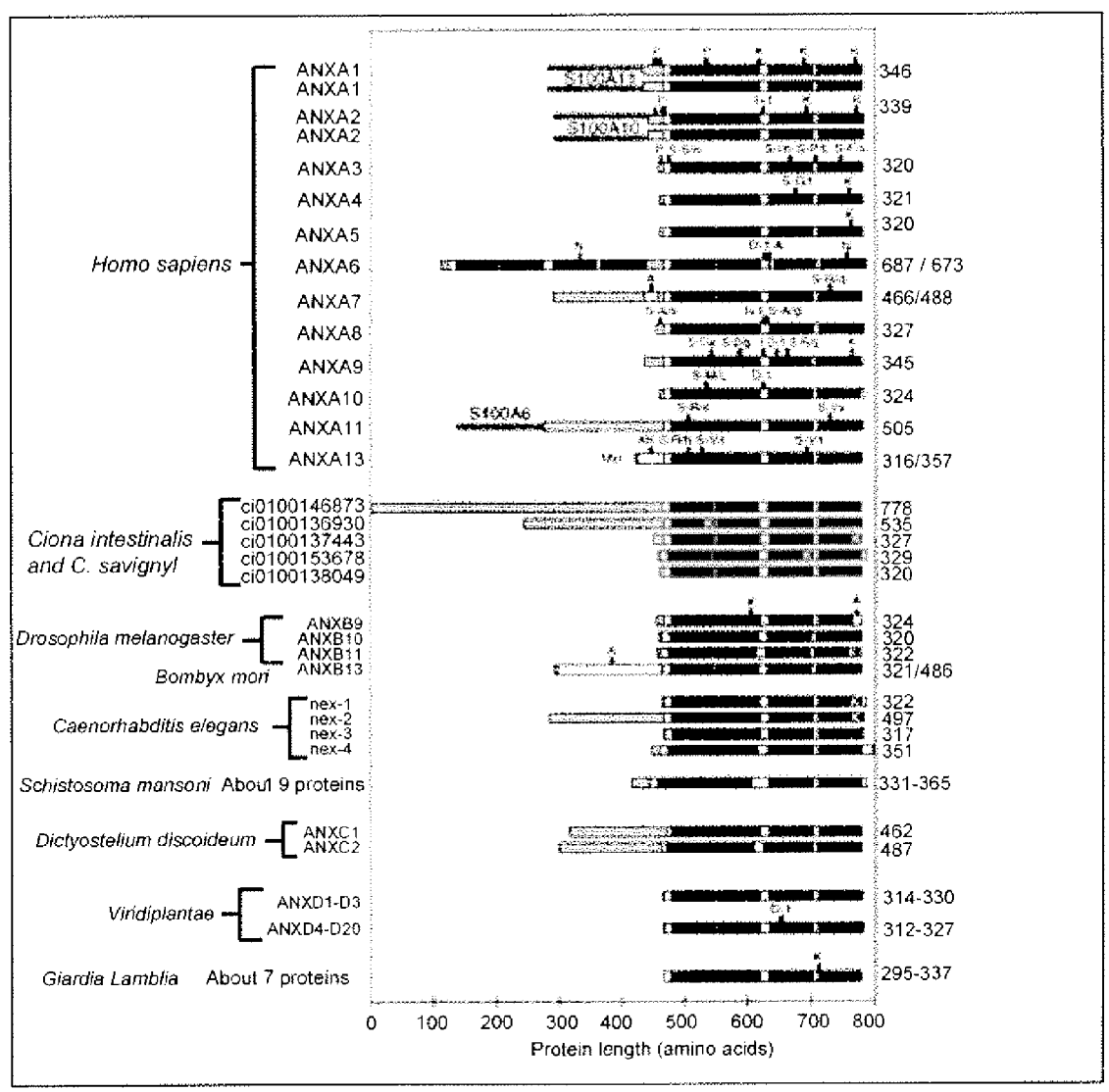
FIG. 6 depicts the domain structures of representative annexin proteins (prior art) in accordance with an embodiment of the present invention. Orthologs of the 12 human annexins shown in other vertebrates have the same structures, with strict conservation of the four repeats in the core region (black) and variation in length and sequence in the amino-terminal regions (shaded). Human ANXA1 and ANXA2 are shown as dimers, with the member of the S100 protein family that they interact with. Domain structures for other model organisms are derived from public data made available by the relevant genome-sequencing projects. Features: S100Ax, sites for attachment of the indicated member of the S100 family of calcium-binding proteins; P, known phosphorylation sites; K, KGD synapomorphy (a conserved, inherited characteristic of proteins); I, codon insertions (+x denotes the number of codons inserted); S-A/b, nonsynonymous coding polymorphisms (SNPs) with the amino acid in the major variant (A) and that in the minor variant (b); N, putative nucleotide binding sites; D, codon deletions (-x denotes the number of codons deleted); A, alternatively spliced exons; Myr, myristoylation. The total length of each protein is indicated on the right.

The annexin family of proteins has been found to be highly homologous. This high homology is also reflected in their structures, which are virtually super imposable from the various annexins. (See FIG. 6.) All annexins have the same membrane binding loops as annexins A5 and B12, and are known to interact in identical ways. Therefore, one of ordinary skill in the art would appreciate the same approach described herein can be applied to all other members of the annexin family without undue experimentation.

In the presence of calcium, only a small number of the more than 300 amino acid residues of annexin directly interact with the membrane while most amino acid residues do not. For example, the N-terminal labeling currently used by existing commercial sources does not come in contact with the membrane. Some of the most deeply membrane penetrating residues in annexin B12 are at positions 101 and 260. The inventor selectively substituted a cysteine at either one or both of the positions in annexin B12 and labeled the protein with polarity-sensitive fluorophores, BADAN and NBD. The fluorescence properties of the resulting annexin derivatives are vastly different depending on whether they are membrane-bound or not. For example, in the case of the BADAN labeled annexin derivatives, membrane interaction upon binding to apoptotic cells increases the fluorescence intensity by more than an order of magnitude. In addition, membrane-interaction causes the maximum of the fluorescence intensity to blue-shift by almost 100 nm. In aqueous solution, the soluble (unbound) BADAN labeled annexin B12 derivative has a low intensity spectrum with a maximum near 530 nm. Accordingly, by monitoring the fluorescence change at ~420 nm to ~470 nm, elimination or substantial elimination of background signal from unbound protein is enabled.

Figure 3:
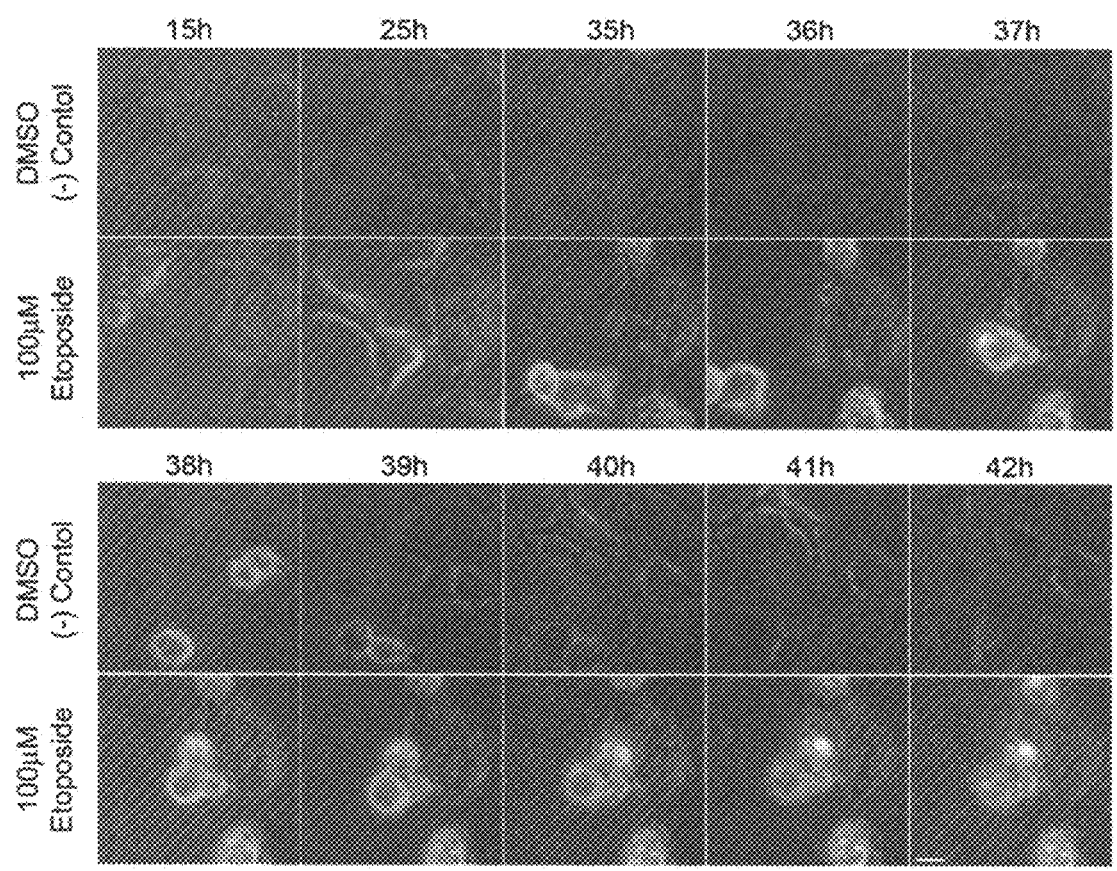
FIG. 3 depicts an application of PS-anx to real-time live-cell imaging of apoptosis in COS-7 cells in accordance with an embodiment of the present invention. The same fields of COS-7 cells were monitored for two days under physiological conditions without the presence of an apoptosis inducing factor (DMSO, (−) control) and in the presence of etoposide by time-lapse microscopy. Shown are merged images of phase contrast, green and red fluorescence channels. Green fluorescence indicated PS-anx binding to the phosphatidylserine exposed on the outer leaflet of the plasma membrane, and red fluorescence indicated propidium iodide (PI) staining of nuclei in cells in late apoptosis, with loss of plasma membrane integrity. (Scale bar, 20 μm)

Because PS-anx emitted little fluorescence in the solution state, its continuous presence in the cell culture media was undetectable until membrane-binding occurred, thereby allowing instantaneous visualization of phosphatidylserine exposure on apoptotic cells. In addition, the combination of live-cell imaging, and PS-anx provided a way to monitor the progression of apoptosis in individual cells, and observe cell-to-cell variations in the responses of neighboring cells to the same environment (see FIG. 3.)

The inventor also showed the application of PS-anx to studying dynamic apoptotic processes in neuronal degeneration. The progressive movement of phosphatidylserine exposure along the axons of degenerating sensory neurons was observed along with sequential punctate staining at some localized areas of phosphatidylserine exposure, which may be an indication of the movement of apoptotic signaling processes through the neuron. Moreover, the inventor observed a diversity of responses to the same apoptotic stimulus in neighboring neurons in regards to the spatiotemporal sequence of phosphatidylserine exposure, indicating further the underlying complexity of different apoptotic signaling pathways, which may play a role in individual neurons, and the importance of analyzing biological processes at the single cell level. The ability to observe these responses, heretofore, has never been described.

Additionally, it was observed that PS-anx binding is reversible, as the cells regain health and phosphatidylserine is restored to the inner leaflet of the plasma membrane, demonstrating that PS-anx is particularly useful for detecting the reversibility of apoptosis under different conditions. Previous reports have also indicated that apoptosis can be reversible at the early stages, under certain conditions. It is shown herein the advantage of using PS-anx in combination with live-cell imaging for these types of studies, particularly because it is non-perturbative and can be used to monitor the fate of a single cell from induction of apoptosis to recovery or cell death. In the example of neuronal degeneration shown herein, apoptosis was induced by NGF deprivation of DRG neurons dependent on tropic support for survival, and neurons that were still in the early stages of apoptosis were rescued by adding back NGF. Because analysis was done on a cell-to-cell basis on localized areas of phosphatidylserine exposure, the inventor was able to distinguish the particular areas of an axon in which apoptotic processes were induced and also the particular areas where apoptosis was reversed. Furthermore, it was observed that induction and rescue of apoptosis occurred at various times in neighboring neurons, indicating that responses involving activation of apoptosis or survival mechanisms are unique to the individual neuron.

In summary, PS-anx provides many advantages over previous annexin-based probes because of its applicability to real-time detection by live-cell imaging methods. A particular advantage is that it allows the investigation of potentially interesting cell-to-cell variations that cannot be observed by other methods that are based on the analysis of whole cell populations. Furthermore, PS-anx provides an unambiguous way to measure health and viability in living cells, directly in the cell of interest, and without perturbing the cellular environment, and can be used as a tool to independently demonstrate whether different cell culture conditions are detrimental to cell health. In addition, because PS-anx has switchable fluorescence states, it is applicable to rapid, high-throughput detection of cell apoptosis by measuring fluorescence intensities on a multiwell-plate reader.

The concept of using protein derivatives with polarity-sensitive fluorophores labeled at sites of membrane interaction can be applicable to other applications as well. For example, small phosphatidylserine-containing microdomains may be exposed on the surface of cells under certain conditions.

In various embodiments, the present invention provides for annexin derivatives, methods for using the annexin derivatives to detect phosphatidylserine exposure, methods for using the annexin derivatives to detect apoptosis, methods of producing the annexin derivatives and kits for the aforementioned methods. The present invention also provides for methods and kits for using the annexin derivatives to detect surviving cells and to monitor cell health.

In various embodiments, the annexin derivative comprises an annexin comprising one or more amino acids conjugated to a polarity sensitive fluorophore, wherein the one or more amino acids were inserted into or substituted at or in close proximity to a polarity changing site on the annexin. Particularly useful amino acids include, but are not limited to, cysteine and lysine. In one embodiment, the annexin from which the annexin derivative is derived is a cysteine-less or lysine-less variant. Deleting or substituting the cysteine or lysine from the wild type annexin may be done at the same time as inserting substituting the one or more amino acids at a polarity changing site of the annexin; or it may be done in separate steps.

Discussions herein regarding amino acids conjugated to a polarity sensitive fluorophore, amino acids labeled with a polarity sensitive fluorophore, fluorophore conjugated amino acids, fluorophore labeled amino acids and the like would be understood that the fluorophore is typically conjugated or labeled onto the amino acid after the insertion or substitution.

In one embodiment, the polarity changing site is a membrane-interaction site on the annexin. Thus, in some embodiments, the annexin derivative comprises: an annexin comprising one or more fluorophore conjugated amino acids (e.g., cysteine, lysine) inserted next to or substituted at or in close proximity to a membrane-interaction residue position on the annexin.

Polarity changes do not require a direct interaction of the fluorophore with the membrane. Indeed, polarity changes could also arise from conformational changes such as secondary, tertiary structural changes as well as the known oligomerization properties of annexins on membranes. Accordingly, in another embodiment, the polarity changing site on the annexin is site on the annexin that undergoes a conformational change. For example, a fluorophore introduced at a contact surface between individual subunits will also experience a change in polarity as annexin B12 oligomerizes upon membrane interaction. Thus, in some embodiments, the annexin derivative comprises: an annexin comprising one or more fluorophore conjugated amino acids (e.g., cysteine, lysine) inserted next to or substituted at or in close proximity to a loop site on the annexin, and a fluorophore. While it is expected that loop sites work best as they are commonly involved in conformational changes, substitution and/or insertion of the one or more amino acids (e.g., cysteine, lysine) are by no means limited to loop sites.

As shown in FIG. 7 for annexin B12, additional positions for substitution or insertion of the one or more amino acids, are positions within the loop sites. These positions include, but are not limited to, residues 26-33, 70-73, 97-105, 141-145, 180-189, 226-229, 256-264, and 301-304. Additionally, with the high homology among annexins, a site homologous to these loop positions in other annexins can be a location for a substitution or insertion of one or more fluorophore labeled amino acids. One of ordinary skill in the art will be able to readily determine homologous sites for insertion or substitution.

The fluorophore on the annexin derivatives of the present invention may be polarity sensitive and labeled on the amino acid (e.g., covalently linked) that was substituted or inserted in the annexin, such as cysteine or lysine. Nearly all fluorophores are sensitive to polarity and thus many other fluorophores may be applicable. Particularly useful fluorophores are thiol-reactive fluorophores. The present fluorophores, in particular BADAN, were chosen simply because they are rather strongly polarity dependent. Particularly useful fluorophores include but are not limited to BADAN, IANBD and other related fluorophores such as prodan and dansyl.

The annexin may be any annexin in the annexin family of proteins. Examples of annexins include, but are not limited to, annexins A1, A2, A3, A4, A5, A6, A7, A8, A9, A10, A11, and A13; annexins ci0100146873, ci0100136930, ci0100137443, ci0100153687, and ci0100138049; annexins B9, B10, B11, and B13; annexins nex-1, nex-2, nex-3, and nex-4; annexins from *Schistosoma mansoni*; annexins C1 and C2; annexins D1-D3, annexins D4-D20; and annexins from *Giardia lamblia*. (See FIG. 6.) One of ordinary skill in the art, without undue experimentation, will be able to readily determine additional annexins that can be used. Particularly useful annexins include but are not limited to annexin B12 and annexin A5.

In embodiments wherein the annexin derivative is derived from annexin B12, the one or more amino acids (e.g., cysteine, lysine) are inserted next to or substituted at a residue position within the A-B and/or D-E loop of each of the four annexin repeat regions of the annexin B12 molecule (see FIG. 8; see e.g., Kim et al., *A helical Haripin Region of Soluble Annexin B12 Refolds and Forms a Continuous Transmembrane Helix at Mildly Acidic pH*. (2005) THE JOURNAL OF BIOLOGICAL CHEMISTRY 280(37):32398-32404, herein incorporated by reference in its entirety as though fully set forth).

In various embodiments, the one or more amino acids (e.g., cysteine, lysine) are inserted next to or substituted at one or more residues among positions 26-33, 70-73, 97-105, 141-145, 180-189, 226-229, 256-264, and 301-304, which are residues within the loop sites in annexin B12. In particular embodiments, the one or more amino acids are inserted next to or substituted at residue position 101, 260 or both. In one particular embodiment, the annexin derivative comprises: an annexin B12 comprising a cysteine substituted at residue position 101, 260 or both, wherein a BADAN or NBD fluorophore is labeled on the cysteine.

In embodiments wherein the annexin derivative is derived from annexin A5, the one or more amino acids (e.g., cysteine, lysine) may be inserted next to or substituted at or around residue position 262.

The aforementioned approach of substituting or inserting one or more polarity sensitive fluorophores labeled amino acids (e.g., cysteine, lysine) on the annexin may also be applicable to other proteins that interact with the membrane; particularly, for proteins that specifically bind to phosphatidylserine-containing membranes, in view of the fact that other proteins also show enhanced binding ability to phosphatidyiserine. Such proteins include but are not limited to C2 domain containing proteins such as synaptotagmin, lactadherin or Factor VIII.

Further based on the inventor's discovery and work, additional embodiments of the present invention provides for membrane-binding protein derivatives with polarity-sensitive fluorophores, methods of using the membrane-binding protein derivatives, methods of producing the membrane-binding protein derivatives, and kits for the aforementioned methods. The signal of bound protein from that of unbound protein may be enhanced for any protein for whatever its membrane interaction specificity may be.

In various embodiments, the membrane-binding protein derivative comprises: a membrane-binding protein comprising one or more fluorophore conjugated amino acids (e.g., cysteine, lysine) inserted next to or substituted at a polarity changing site on the membrane-binding protein. In one embodiment, the membrane-binding protein is a cysteine-less or lysine-less variant.

In one embodiment, the polarity changing site is a membrane-interaction site on the membrane-binding protein. Thus, in some embodiments, the membrane-binding protein derivative comprises: a membrane-binding protein comprising one or more fluorophore conjugated amino acids inserted next to or substituted at or in close proximity to a membrane-interaction residue position on the membrane-binding protein.

As noted above, polarity changes do not require a direct interaction of the fluorophore with the membrane. Accordingly, in another embodiment, the polarity changing site on the membrane-binding protein is a conformational changing site on the membrane-binding protein. Thus, in some embodiments, the membrane-binding protein derivative comprises: a membrane-binding protein comprising one or more fluorophore conjugated amino acids inserted next to or substituted at or in close proximity to a loop site on the membrane-binding protein. Again, while it is expected that loop sites work best, substitution and/or insertion of the one or more amino acids are by no means limited to loop sites.

The fluorophore on the membrane-binding protein derivatives of the present invention may be labeled on the one or more amino acids (e.g., covalently linked) that were substituted or inserted into the annexin, such as cysteine or lysine. The fluorophore may be ones as described above.

In various embodiments, the present invention provides for a method for detecting apoptosis, comprising: providing an annexin derivative of the present invention, contacting (e.g., applying) the annexin derivative to a sample comprising cells, and detecting a fluorescence of the sample. Contacting the annexin derivative to the sample is performed in the presence of calcium. In various embodiments, detecting a fluorescence comprises detecting an increase in fluorescence intensity; particularly, an increase in fluorescence intensity by one or more orders of magnitude. In other embodiments, detecting a fluorescence comprises detecting a shift in the wavelength of the fluorescence. In embodiments wherein the fluorophore on the annexin derivative is BADAN, detecting the fluorescence of the sample may comprise detecting the fluorescence in the blue light range (e.g., about 430 nm or about 420-470 nm). In embodiments wherein the fluorophore on the annexin derivative is NBD, detecting the fluorescence of the sample may comprise detecting an increase in fluorescence intensity (particularly, an increase in fluorescence intensity by one or more orders of magnitude) at about 500 nm to about 600 nm, or about 500 nm to about 530 nm. In one particular embodiment, the $\lambda_{MAX}$ of the protein in solution is about 540 nm and the $\lambda_{MAX}$ of the membrane-bound protein is about 520 nm. Thus, detecting the fluorescence of the sample to detect apoptosis may comprise detecting the fluorescence at a $\lambda_{MAX}$ of about 520 nm.

In further embodiments, the method of detecting apoptosis may be used to detect individual cells undergoing apoptosis in a cell population. For instance, the population of cells may be viewed under a microscope and individual cells undergoing apoptosis can be viewed and distinguished from healthy cells.

In another embodiment, the present invention provides for a method for detecting phosphatidylserine exposure, comprising: providing an annexin derivative of the present invention, contacting (e.g., applying) the annexin derivative to a sample comprising cells, and detecting a fluorescence of the sample as described above. Similarly, the method may be used to detect individual cells that are exposing phosphatidylserine in a cell population, as described above.

In a further embodiment, the method comprises detecting the fluorescence of the sample in real time. In another embodiment, the method further comprises detecting the fluorescence of the sample in a high-throughput screening system.

The annexin derivatives of the present invention may also be used to detect the presence of surviving cells or to monitor cell health. In experimental procedures, it may be beneficial to continuously monitor the health of individual cells within a culture. For instance, in a cell culture containing an annexin derivative of the present invention, a user (e.g., a researcher) may observe that a few cells in the culture are undergoing apoptosis and can remove those cells, or the user can factor in that information in her analysis of the experiment (e.g., quality control). For example, if a cell is undergoing apoptosis, the user may choose to not include the cell in her data set. A user may also choose to administer a therapeutic drug to rescue cells as they are going down the apoptosis pathway.

In various embodiments, the present invention provides for a method for detecting surviving cells, comprising: providing an annexin derivative of the present invention, contacting (e.g., applying) the annexin derivative to a sample comprising cells, and detecting a substantial lack of fluorescence or the lack of a shift in the fluorescence in the sample. Applying the annexin derivative to the sample is performed in the presence of calcium. In another embodiment, the annexin derivative is added to cell culture media that used to culture the cells. Detecting a substantial lack of fluorescence refers to the lack of a detectable increase in fluorescence intensity; for example, the lack of an increase of one or more orders of magnitude in the fluorescence intensity. In embodiments wherein the fluorophore on the annexin derivative is BADAN, detecting the lack of a shift in the fluorescence of the sample may comprise detecting the lack of a fluorescence in the blue light range (e.g., about 430 nm or about 420-470 nm); e.g., not observing a fluorescence in the blue light range. That is, the fluorescence of BADAN does not blue shift. In embodiments wherein the fluorophore on the annexin derivative is NBD, detecting the substantial lack fluorescence of the sample may comprise detecting an absence of an increase in fluorescence intensity at about 500 nm to about 600 nm, or about 500 nm to about 530 nm. Since the $\lambda_{MAX}$ of the protein in solution is about 540 nm and the $\lambda_{MAX}$ of the membrane-bound protein is about 520 nm, detecting the substantial lack of fluorescence of the sample may comprise detecting the substantial lack of fluorescence at a $\lambda_{MAX}$ of about 520 nm. That is, the fluorescence will not shift.

In a further embodiment, the method comprises detection of surviving cells in the sample in real time. In another embodiment, the method further comprises detection of the surviving cells in the sample in a high-throughput screening system.

In additional embodiments, the method of detecting surviving cells may be used to detect individual cells in a cell population. For instance, the population of cells may be viewed under a microscope and individual cells that are healthy can be distinguished from a cell that is undergoing apoptosis.

In another embodiment, the present invention provides for a method of monitoring cell health comprising: providing an annexin derivative of the present invention, contacting the annexin derivative to a sample comprising cells; and monitoring the fluorescence, wherein an increase in the fluorescence intensity and/or a shift in the wavelength of the fluorescence indicate that a cell is undergoing apoptosis and an absence of an increase in the fluorescence intensity and/or an absence of a shift in the wavelength of the fluorescence indicate that a cell is healthy. In additional embodiments, monitoring the fluorescence comprises detecting the fluorescence or a substantial lack of fluorescence as described above. In a further embodiment, the method comprises administering a therapeutic drug upon detection of apoptotic cells as described above. In another embodiment, monitoring is performed in real time and/or in a high-throughput screening system.

In additional embodiments, the method of monitoring cell health may be used to distinguish between an individual apoptotic cell and an individual healthy cell in a cell population. For instance, the population of cells may be viewed under a microscope and a cell that is healthy can be distinguished from a cell that is undergoing apoptosis.

The present invention is also directed to a kit to detect phosphatidylserine exposure, detect apoptosis, detect surviving or healthy cells and/or to monitor cell health. The kit is an assemblage of materials or components, including at least one of the annexin derivatives of the present invention. In another embodiment, the kit may include cell culture media containing one of the annexin derivatives of the present invention. The exact nature of the components configured in the inventive kit depends on its intended purpose. For example, some embodiments are configured for the purpose of detecting mammalian apoptotic cells and/or surviving mammalian cells. In another embodiment, the kit is configured particularly for the purpose of detecting human apoptotic cells and/or surviving human cells. In further embodiments, the kit is configured for detecting apoptotic cells and/or surviving cells from farm animals, domestic animals, and laboratory animals. In other embodiments, the kit may be configured for the purpose of real time apoptosis detection, real time detection of surviving cells, high throughput apoptosis screening, and/or high throughput screening of surviving cells.

Instructions for use may be included in the kit. "Instructions for use" typically include a tangible expression describing the technique to be employed in using the components of the kit to effect a desired outcome, such as to detect phosphatidylserine exposure, to detect apoptotic cells, to detect healthy cells, and to monitor cell health. Instructions for use may include, but are not limited to, one or more instructions selected from the following: applying a culture medium comprising the annexin derivative to a sample comprising cells; apply the annexin derivative to a sample comprising cells; apply the annexin derivative to a sample comprising cells in the presence of calcium; detect a fluorescence of the sample; and detect fluorescence in the blue light range if the fluorophore on the annexin derivative is BADAN. In embodiments wherein the kit is for the detection of surviving cells, the instructions may comprise detecting a substantial lack of fluorescence. Instructions for use may also include instructions to detect the fluorescence of the cells in real time or instructions to detect the fluorescence of the cells in a high-throughput screening system.

Optionally, the kit also contains other useful components, such as, quantities of calcium, diluents, buffers, slides, test tubes, multi-well plates, syringes, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in apoptosis detection. As used herein, the term "package" refers to a suitable solid matrix or material such as glass, plastic, paper, foil, and the like, capable of holding the individual kit components. Thus, for example, a package can be a glass vial used to contain suitable quantities of the annexin derivative of the present invention. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Only small amounts of annexin B12 were necessary. In order to test how much annexin B12 is needed to give the signal, different amounts of labeled annexin B12 were added to cells (data not shown). As little as 100 ng of the annexin B12 derivatives gave strong signals.

Example 2

The inventor has worked out conditions to produce large quantities of labeled annexin B12 and have methods to purify it to homogeneity. The expression and purification of single or multi cysteine-containing annexin B12 derivatives has been described previously by the inventor in a number of studies on this protein. The recombinant annexin B12 lacks the two endogenous cysteine residues which were replaced with alanine (C113A/C303A). The single cysteine mutants at positions 101 and/or 260 were generated using standard mutagenesis and protein purification methods as described in Langen et al. J. BIOL. CHEM., 273:22453-22457 (1998). The mutations were tolerated well. Purified annexin B12 mutants were stored at −70° C. in Hepes buffer (20 mM, pH 7.4) containing NaCl (100 mM) and dithiothreitol (1 mM) or used directly. Labeling with the fluorophores (purchased from Invitrogen) was performed by incubating the protein (typically at micromolar concentrations) with 10 fold excess of the respective labels. The labeling reaction was quenched using β-mercaptoethanol, whose concentration was twice that of the label (i.e., 20 fold higher than that of the protein). The labeled protein was purified using gel filtration and the resulting protein was free of unattached fluorophore.

Example 3

Protein Purification and Labeling

Cysteine mutations were placed in the appropriate sites in Cys-less variants of AnxA5 (C316A) and AnxB12 (C113A-C302A) (Mailliard et al., (1997) BIOCHEMISTRY 36, 9045-9050) plasmids by site-directed mutagenesis (QuickChange, Stratagene). All mutations were verified by DNA sequencing. The AnxB12 and AnxA5 mutants were expressed in DH5α *Escherichia coli* and purified by reversible $Ca^{2+}$-dependent biding to phospholipid vesicles followed by gel filtration as described previously (Mailliard et al., (1997) BIOCHEMISTRY 36, 9045-9050; Langen et al., (1998) J. BIOL. CHEM. 273, 22453-22457). Unlabeled proteins were stored in 20 mM Hepes containing 100 mM NaCl (Hepes-NaCl) and 1 mM dithiothreitol at pH 7.4. Protein concentrations were measured by absorbance at 280 nm and use of the appropriate extinction coefficients ($\epsilon$=12,288 $M^{-1}$ $cm^{-1}$ for AnxB12 and $\epsilon$=21,110 $M^{-1}$ $cm^{-1}$ for AnxA5).

Prior to labeling, dithiothreitol was removed from the buffer by gel filtration using PD-10 columns (GE Healthcare). The proteins were eluted with Hepes-NaCl buffer and reacted with a 10-fold molar excess of N,N'-Dimethyl-N-(iodoacetyl)-N'-(7-nitrobenz-2-oxa-1,3-diazol-4-yl)ethylenediamine (IANBD, FIG. 1B) or 6-Bromoacetyl-2-dimethylaminonaphthalene (BADAN, FIG. 1C) at the introduced cysteine sites (~2 h at room temperature or overnight at 4° C.). Labeling was quenched with a 2-fold molar excess of β-mercaptoethanol and labeled proteins were eluted with a PD-10 column in Hepes-NaCl. Final protein concentrations after labeling were measured by the BCA assay (Pierce).

Example 4

In Vitro Membrane Binding Assay

Large unilamellar vesicles (LUVs) containing 100% 1-palmitoyl-2-oleoyl-sn-glycero-3-phosphocholine (POPC) or 25% 1-palmitoyl-2-oleoyl-sn-glycero-3-[phospho-L-serine] (POPS)-75% POPC (Avanti Polar Lipids) were prepared as described previously (Reeves and Dowben (1969) J. CELL. PHYSIOL. 73, 49-60). 20 µg of annexin protein was diluted in 500 µl of Hepes-NaCl buffer containing $Ca^{2+}$ (50 µM-3 mM) and mixed with 400 µg of lipid (1:1000 molar ratio) to induce binding. The mixtures were loaded into a 1 cm path-length quartz cuvette, and fluorescence emission was measured in a Jasco FP-6500 spectrofluorometer. The excitation wavelength used for IANBD was set to 478 nm, and fluorescence emission was monitored from 480-650 nm. For BADAN, the excitation wavelength was set to 380 nm, and fluorescence emission was monitored from 400-650 nm.

Example 5

COS-7 Cell Culture

COS-7 cells were cultured in Dulbecco's modified Eagle's medium (DMEM) supplemented with 10% fetal bovine serum (FBS) and 100 U/ml penicillin and 100 μg/ml streptomycin and grown on tissue culture plates 24 h-48 h prior to live-imaging experiments. Apoptosis was induced in COS-7 cells by 100 μm etoposide and compared with healthy cells grown without the addition of etoposide (DMSO only).

Example 6

Primary Neuron Cultures

Dorsal Root Ganglion Neurons were isolated and purified as previously described (Rosenberg et al., 2008). Briefly DRG neurons from E13-15 Sprague-Dawley rats were dissociated, plated, and purified on collagen-coated tissue culture plates in the presence of NGF (100 ng/ml) for 7 days prior to imaging. Neurons were grown in etched wells in order to limit the orientation of axon growth along a single axis. Apoptosis was induced by removal of NGF from the culture media. For rescue of neuronal degeneration, NGF was added back (100 ng/ml) after 7, 10 and 15 hrs of deprivation.

Example 7

Time-Lapse Microscopy and Live-Cell Imaging

Time-lapse microscopy was performed on an Axiovert 200 motorized inverted microscope equipped with a complete incubation system (Zeiss, Germany). Time-lapse images of COS-7 cells were taken with the AxioCam MRm digital camera from (Zeiss). In order to minimize phototoxicity, neurons were imaged with a Cascade: 1K camera from Photometrics, which reduced exposure times. All images were processed using Axiovision 4.7 software (Zeiss). Cells were imaged in the presence of PS-anx (5-10 μg/ml) and propidium iodide (1 μM) in the culture media by time-lapse microscopy.

Example 8

Structure-Based Design of a Fluorescent Polarity Sensitive Biosensor

Figure 1:
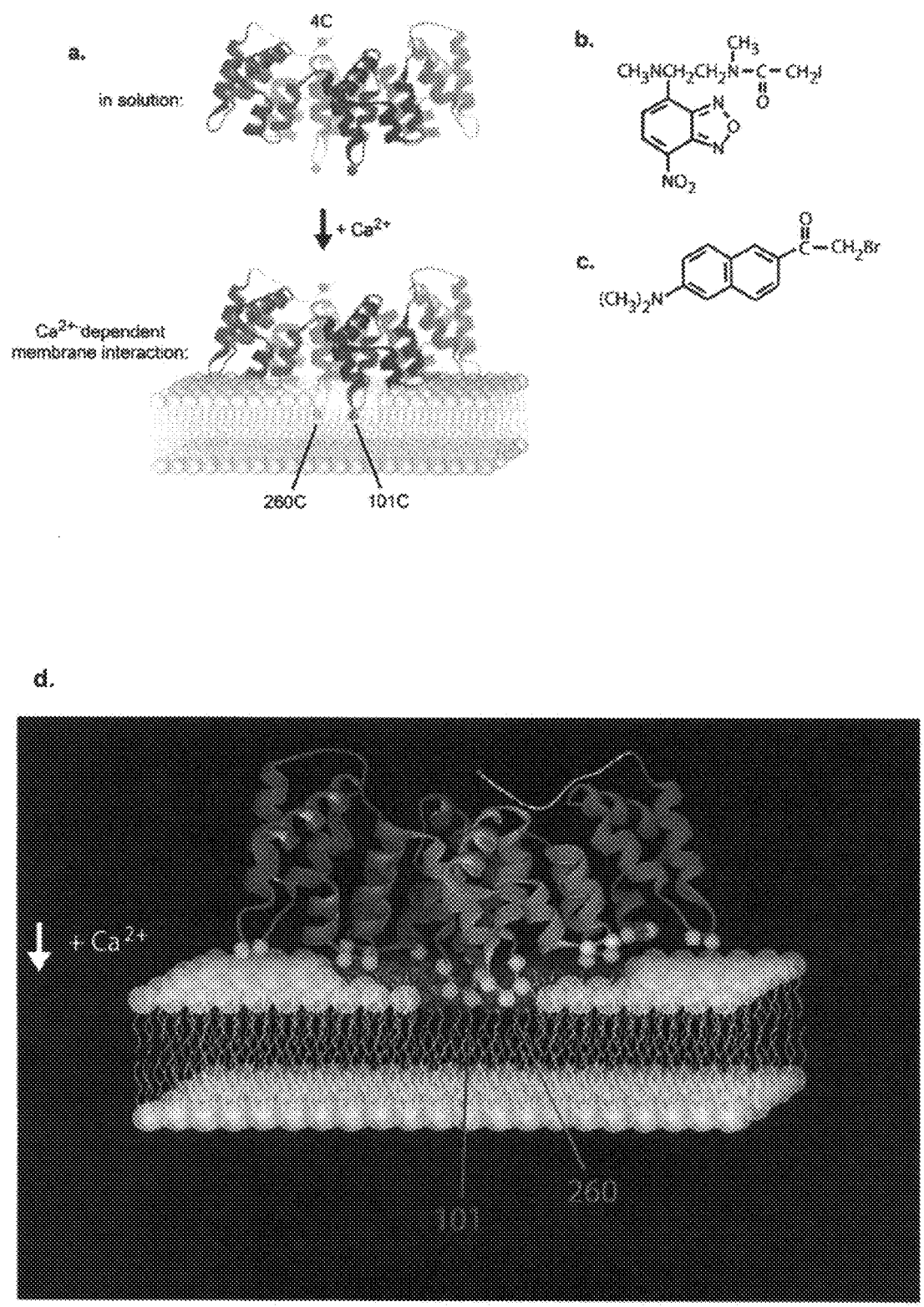
FIGS. 1a-1d depicts the structure-based design of annexin biosensors in accordance with an embodiment of the present invention. (a) A representation of anxB12 (crystal structure) interaction with negatively charged membranes in the presence of $Ca^{2+}$ is shown with the location of tested sites (red spheres on Cα) in the membrane binding loops (101C, 260C) used to create PS-anx. Residue 4C was also tested as a negative control since its location in the N-terminal tail on the concave side of the protein is expected to stay fully exposed to the aqueous environment in both the solution and membrane-bound states. (b) Structures of polarity sensitive label N,N'-Dimethyl-N-(iodoacetyl)-N'-(7-nitrobenz-2-oxa-1,3-diazol-4-yl)ethylenediamine (IANBD). (c) Structures of polarity sensitive label 6-Bromoacetyl-2-dimethylaminonaphthalene (BADAN). The thiol-reactive labels were attached to annexin via cysteines which were placed at the specified residue positions by site-directed mutagenesis. (d) Another view of the structure of annexin B12 is depicted to highlight potential membrane interaction sites (yellow spheres; all are located in membrane-facing loop regions).

In order to design a probe more suited for live-cell imaging applications, PS-anx was engineered based on the structure of the $Ca^{2+}$-dependent membrane-bound state. Polarity sensitive labels were placed in the loop regions which mediate $Ca^{2+}$-dependent membrane interactions, transitioning from a polar (aqueous solution) to a nonpolar (lipid membrane) environment upon membrane binding (FIG. 1a). The inventor chose residues at positions 101 and 260 as the labeling sites, for their ideal location in the membrane-binding loops (FIG. 1a). In addition to AnxB12 labeled with a single polarity sensitive fluorophore, a double-labeled AnxB12 molecule was created with fluorophores attached at both 101 and 260, in order to increase the brightness of the probe. Because annexin A5 (anxA5, also known as annexin V) has already been widely used and characterized for apoptosis assays, position 262 in AnxA5, a site homologous to residue 260 in AnxB12, was also tested. As a negative control, residue position 4 in AnxB12 was labeled to confirm that detected changes in fluorescence were directly a result of membrane interaction (FIG. 1a).

Polarity-sensitive molecules that emit increased fluorescence intensity in nonpolar environments were screened and two thiol-reactive labels: N,N'-Dimethyl-N-(iodoacetyl)-N'-(7-nitrobenz-2-oxa-1,3-diazol-4-yl)ethylenediamine (IANBD, FIG. 1b) and 6-Bromoacetyl-2-dimethylaminonaphthalene (BADAN, FIG. 1c) were chosen.

Example 9

Validation by In Vitro Fluorescence Assays

In order to determine the exact differences in fluorescence between the solution and membrane-bound states the fluorescence intensities of these annexin-based polarity sensitive biosensors were measured in an in vitro binding assay. Membrane binding was induced by the presence of phosphatidylserine-containing vesicles in neutral buffer containing $Ca^{2+}$. As expected, the fluorescence intensity was negligible for all the labeled annexins free in solution (FIG. 2a-l, dashed lines), and for AnxB12 4C-IANBD (FIG. 2a) and AnxB12 4C-BADAN (FIG. 2f) in both the solution and membrane-bound states. For AnxB12 101C-IANBD, AnxB12 260C-IANBD, AnxA5 262C-IANBD (FIG. 2b-d) considerable increases in fluorescence intensities were measured in addition to a slight blue shift from an emission maximum at 540 nm in the solution state to 525 nm in the membrane-bound state. Fluorescence emission measured for the double-labeled AnxB12 101C-, 260C-IANBD in the membrane-bound state was substantially brighter, with only a negligible increase in the background fluorescence of the solution state (FIG. 2e). Based on the typical emission profiles of conventional filter sets for FITC/green fluorescence, the fluorescence emissions between 500-550 nm (shaded column, FIG. 2e) were quantified, revealing a ~45-fold increase in the membrane-bound AnxB12 101C-, 260C-IANBD when compared to the solution state.

Slightly lower fluorescence intensities were measured for the BADAN labeled annexins at corresponding sites (FIG. 2g-j); however a large blue shift was observed from an emission maximum of 530 nm in the solution state to 450 nm in the membrane-bound state, which may be used to design custom filters, which cut off most of the background fluorescence of the solution state while maximizing the emitted fluorescence of the membrane-bound state. For example, an analysis of the fluorescence emission intensities between 420-470 nm (shaded column, FIG. 2j) resulted in a ~100-fold increase in fluorescence of the membrane-bound AnxB12-101C-260C-BADAN compared to the solution state.

For the various PS-anx probes tested (FIG. 2), there was no detectable loss in membrane binding ability of the annexin protein, as judged by co-sedimentation with phosphatidylserine-containing vesicles (data not shown). This was further supported by fluorescence measurements performed at various $Ca^{2+}$ concentrations, which indicated that membrane binding was optimal in a wide range of concentrations, from 100 μM to 3 mM $Ca^{2+}$ at neutral pH.

Thus, attachment of polarity sensitive labels IANBD and BADAN to residues in the membrane binding loops provided an effective way to generate annexin derivatives with built-in "on" and "off" fluorescence states, in a range of excitation and emission wavelengths. In addition both IANBD-(green fluorescence) and BADAN-(blue fluorescence) labeled annexins may be used with conventional filter sets equipped on most fluorescence microscopes.

Example 10

Application to Live-Cell Imaging

PS-anx was tested for suitability for live-cell imaging. In order to test its capacity to specifically highlight cells undergoing apoptosis, PS-anx was added directly to the culture media of COS-7 cells induced to undergo apoptosis by etoposide, a known apoptotic factor. The cells were monitored under physiological conditions (37° C., 5% $CO_2$) by time-lapse microscopy. Both IANBD- and BADAN-labeled variants of PS-anx and observed similar results were tested (data not shown). Therefore, AnxB12 101C-, 260C-IANBD (referred to as PS-anx) were used for all subsequent cell culture experiments based on its enhanced brightness (FIG. 2e). In addition to higher fluorescence intensities, IANBD has the advantage of being excitable in the visible light spectrum, thereby avoiding the potentially harmful UV spectrum. As the inventor expected, it was observed bright PS-anx staining of COS-7 cells in the early stages of apoptosis (FIG. 3) and a gradual increase in staining concurrent with progression into final cell death, marked by PI staining. In comparison, no annexin or PI staining was observed in COS-7 cells growing under normal conditions, confirming that PS-anx binding and fluorescence was specific to apoptotic cells. Furthermore the background fluorescence from the solution state was close to undetectable. To confirm that the presence of PS-anx in the culture media did not perturb the cellular environment, COS-7 cells were cultured in the presence and absence of PS-anx and did not observe any differences in the cell growth rate (data not shown). Thus, the use of PS-anx in combination with live-cell imaging provides a way to continuously monitor the progression of apoptosis in living cells without perturbing the cellular environment.

Example 11

Application to Neuronal Degeneration

Having established the utility of PS-anx in live-cell imaging of a simple model system, the inventor explored whether it could be used to provide insights in a more complex apoptotic process, such as in neuronal degeneration. One of the interesting features is that under different conditions, axonal degeneration and cell body death can occur at different times and sometimes independently from each other. PS-anx was used to study apoptotic processes in sensory neurons of the Dorsal Root Ganglion (DRG).

Because the DRG neurons were dependent on tropic support for survival, apoptosis was induced by deprivation of nerve growth factor (NGF) and monitored by time-lapse microscopy. Similar to what was observed in COS-7 cells, a time lag of several hours was observed between initial phosphatidylserine exposures in the axons and complete cell death, indicated by PI staining of the cell bodies. PS-anx staining was observed in both axons and cell bodies of NGF-deprived neurons (FIG. 4b) and little PS-anx fluorescence was observed in neurons grown in the presence of NGF (FIG. 4a). A gradual increase in fluorescence in NGF-deprived neurons was observed, corresponding to both a gradual increase in amount of phosphatidylserine exposure in an individual neuron and also the number of degenerating neurons present over longer periods of NGF deprivation (FIG. 4b). Furthermore, annexin binding occurred in a specific spatiotemporal order, indicating that phosphatidylserine exposure occurs successively, originating from a particular location in the axon and spreading toward the cell body or the axon terminal (FIG. 4c). A closer look at phosphatidylserine exposure on a single axon revealed a dynamic, sequential punctate staining pattern (FIG. 4d) which may be an indication of the underlying biological processes involved in axonal degeneration. Furthermore, phosphatidylserine exposure on the cell bodies was generally observed immediately prior to complete loss of membrane integrity and final cell death, indicated by PI staining.

Example 12

Rescue of Neuronal Degeneration

Previous reports have indicated that the initiation of apoptosis does not necessarily indicate a commitment to cell death, therefore the inventor addressed whether PS-anx could be used to visualize rescue of apoptosis in neurons.

Figure 4:
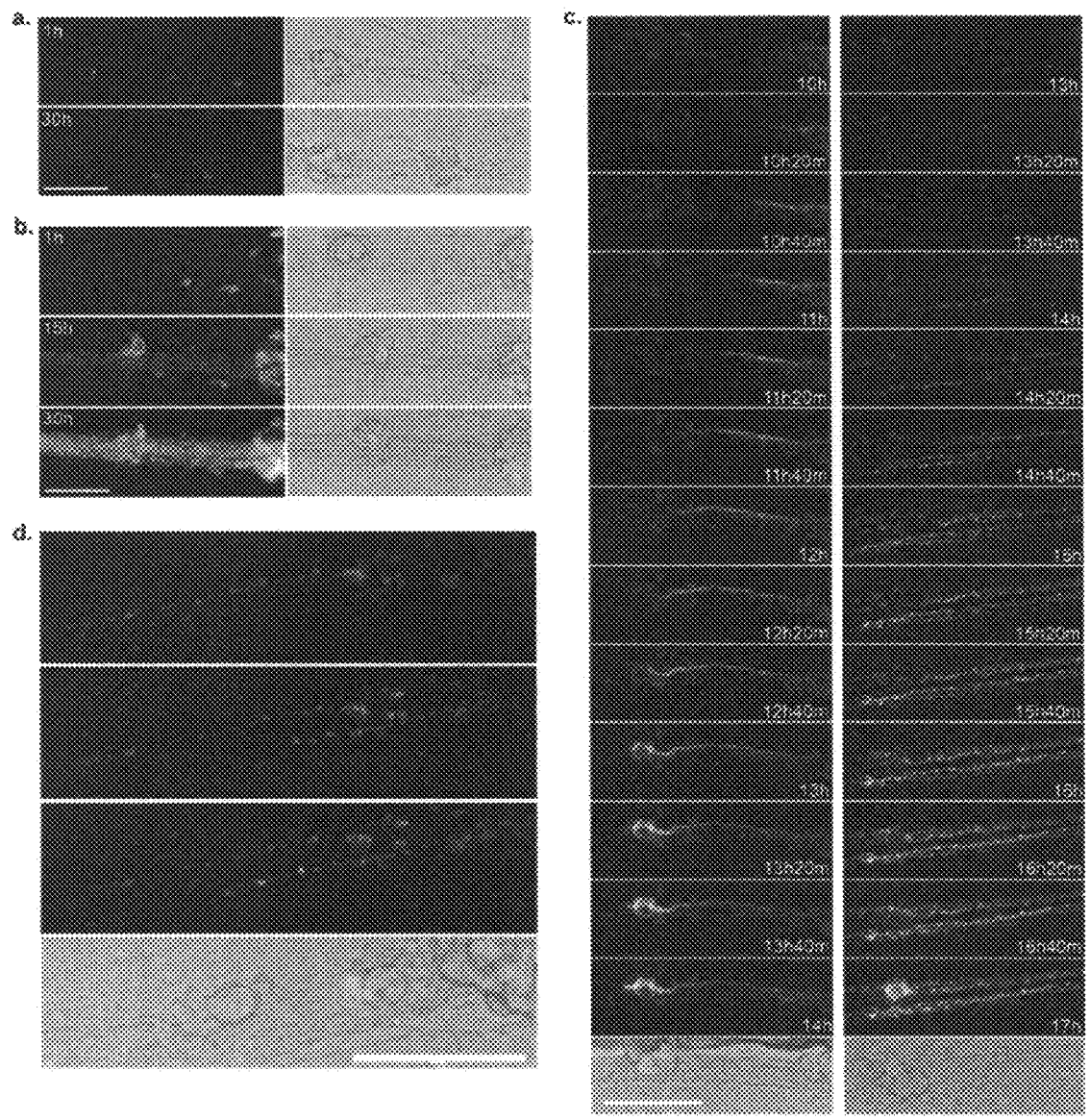
FIGS. 4a-d depicts an application of PS-anx to monitoring the degeneration of DRG neurons in accordance with an embodiment of the present invention. Time-lapse microscopy was used to image dorsal root ganglion (DRG) neurons (a) in normal physiological conditions and (b) under nerve growth factor (NGF) deprivation; left panels show green fluorescence (PS-anx) and right panels show merged images of phase contrast, green and red (PI) fluorescence. (c) Time-lapse images showing the progressive movement of apoptotic phosphatidylserine exposure along single axons to cell bodies. (d) Localized progression of phosphatidylserine exposure along a single axon shown at 20 minute intervals revealing a punctate staining pattern of PS-anx. Merged images in c-d show the overlay of phase contrast, green and red fluorescence of the last time point shown. The times shown indicate the time after NGF was removed (b-d) or replaced (a) in fresh media. (Scale bars, 100 μm)
Figure 5:
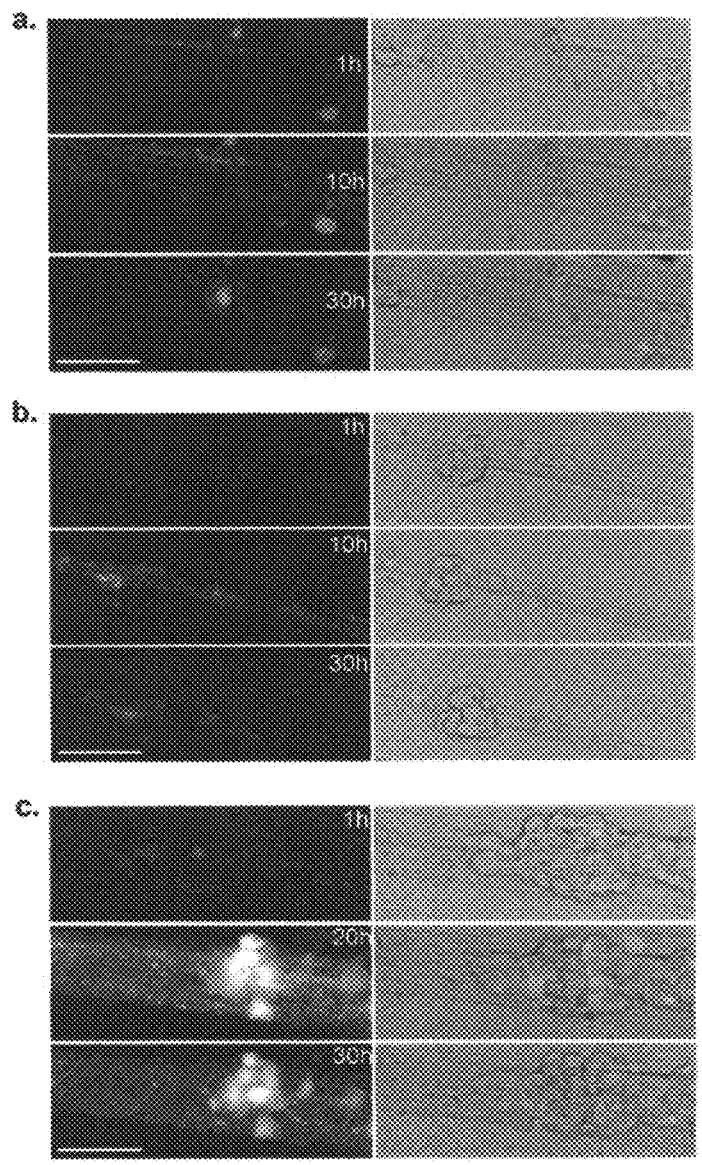
FIGS. 5a-c depicts a rescue of neuronal degeneration visualized by PS-anx. DRG neurons dependent on tropic support were induced to undergo apoptosis by deprivation of NGF for (a) 7, (b) 10, or (c) 15 hours before NGF was re-added to the culture media. Time lapse images showed PS-anx binding reversed in some but not all axons, while PS-anx staining of cell bodies were retained, indicating that rescue was possible in certain neurons in which phosphatidylserine exposure had not progressed to the cell bodies (late-stage). Left panels show green fluorescence (PS-anx) and right panels show merged images of phase contrast, green and red (PI) fluorescence. The times shown indicate the time after initial NGF removal. (Scale bars, 100 μm)

Apoptosis in DRG neurons were induced by deprivation of NGF, and NGF was subsequently added back after observing the initiation of phosphatidyiserine exposure in some axons by PS-anx fluorescence (~7-15 h after initial NGF removal). Complete degeneration was blocked by the re-addition of NGF in some cells but not all (FIG. 5). Because the initiation of apoptotic processes occurred at different times after NGF withdrawal in individual neurons, the inventor deduced that rescue was observed in neurons which were still in an early stage of apoptosis. In general, rescue was observed in neurons with PS-anx stained axons, but not in neurons with PS-anx stained cell bodies (FIG. 5), which was generally observed to occur later (FIG. 4). Also, some axons retained PS-anx staining, indicating that at some intermediate stage of apoptosis, no rescue was possible. Finally, in addition to showing that initial apoptotic processes (phosphatidylserine exposure) in degenerating axons were reversible, it was also verified that PS-anx binding reversed, as the neuron regains health and phosphatidylserine is restored to the inner leaflet of the plasma membrane.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. An annexin derivative, comprising:
the amino acid sequence of SEQ ID NO: 1 wherein residues 101 and 260 of SEQ ID NO: 1 have been substituted with cysteine residues, wherein said cysteine residues are conjugated to polarity sensitive fluorophore N,N'-Dimethyl-N-(iodoacetyl)-N'(7-nitrobenz-2-oxa-1,2-diazol-4-yl)ethylenediamine (IANBD) or 6-Bromoacetyl-2-dimethylaminonaphthalene (BADAN), and wherein residues 113 and 302 of SEQ ID NO: 1 are substituted with an amino acid other than cysteine or lysine.

2. The annexin derivative of claim 1, wherein the polarity sensitive fluorophore is N,N'-Dimethyl-N-(iodoacetyl)-N'(7-nitrobenz-2-oxa-1,2-diazol-4-yl)ethylenediamine (IANBD).

3. The annexin derivative of claim 1, wherein the polarity sensitive fluorophore is 6-Bromoacetyl-2-dimethylaminonaphthalene (BADAN).

4. A method of detecting apoptosis, comprising: contacting the annexin derivative of claim 1 to a sample comprising cells; and detecting a fluorescence resulting from the fluorophore in the sample.

5. The method of claim 4, wherein detecting the fluorescence comprises detecting an increase of fluorescence intensity and/or a shift in the wavelength of the fluorescence.

6. The method of claim 5, wherein the increase of fluorescence intensity is one or more orders of magnitude.

7. The method of claim 5, wherein the polarity sensitive fluorophore is N,N'-Dimethyl-N-(iodoacetyl)-N'(7-nitrobenz-2-oxa-1,2-diazol-4-yl)ethylenediamine (IANBD) and the fluorescence is detected at a $\lambda_{max}$ of about 500 to about 600 nm.

8. The method of claim 7, wherein detection is performed in a real time fluorescence detection and/or performed in a high-throughput screening system.

9. The method of claim 5, wherein the polarity sensitive fluorophore is 6-Bromoacetyl-2-dimethylaminonaphthalene (BADAN) and the fluorescence is detected in the blue light range from 420 nm to 470 nm.

10. The method of claim 9, wherein the detection of the fluorescence is performed in a real time fluorescence detection and/or in a high-throughput screening system.

11. A method of monitoring cell health, comprising:
contacting the annexin derivative of claim 1 to a sample comprising cells; and
monitoring the fluorescence resulting from the fluorophore, wherein an increase in the fluorescence intensity and/or a shift in the wavelength of the fluorescence indicate that a cell is undergoing apoptosis and an absence of an increase in the fluorescence intensity and/or an absence of a shift in the wavelength of the fluorescence indicate that a cell is healthy.

12. The method of claim 11, further comprising administering a therapeutic drug upon detection of one or more cells undergoing apoptosis.

13. The method of claim 11, wherein the polarity sensitive fluorophore is N,N'-Dimethyl-N-(iodoacetyl)-N'(7-nitrobenz-2-oxa-1,2-diazol-4-yl)ethylenediamine (IANBD).

14. The method of claim 13, wherein detection is performed in a real time fluorescence detection and/or in a high-throughput screening system.

15. The method of claim 11, wherein the polarity sensitive fluorophore is 6-Bromoacetyl-2-dimethylaminonaphthalene (BADAN).

16. A kit comprising: an annexin derivative comprising the amino acid sequence of SEQ ID NO:1 wherein residues 101 and 260 of SEQ ID NO:1 have been substituted with cysteine residues and said cysteine residues are conjugated to a polarity sensitive fluorophore N,N'-Dimethyl-N-(iodoacetyl)-N' (7-nitrobenz-2-oxa-1,2-diazol-4-yl)ethylenediamine (IANBD) or 6-Bromoacetyl-2-dimethylaminonaphthalene (BADAN), and wherein residues 113 and 302 of said SEQ ID NO:1 are substituted with an amino acid other than cysteine or lysine; and instructions for using the annexin derivative to detect phosphatidylserine exposure.

17. The kit of claim 16, wherein the annexin derivative is in a cell culture medium.

\* \* \* \* \*

SEQUENCE LISTING

```
<160> NUMBER OF SEQ ID NOS: 1

<210> SEQ ID NO 1
<211> LENGTH: 316
<212> TYPE: PRT
<213> ORGANISM: Hydra vulgaris

<400> SEQUENCE: 1

Met Val Val Gln Gly Thr Val Lys Pro His Ala Ser Phe Asn Ser Arg
1               5                   10                  15

Glu Asp Ala Glu Thr Leu Arg Lys Ala Met Lys Gly Ile Gly Thr Asp
            20                  25                  30

Glu Lys Ser Ile Thr His Ile Leu Ala Thr Arg Ser Asn Ala Gln Arg
        35                  40                  45

Gln Gln Ile Lys Thr Asp Tyr Thr Thr Leu Phe Gly Lys His Leu Glu
    50                  55                  60

Asp Glu Leu Lys Ser Glu Leu Ser Gly Asn Tyr Glu Ala Ala Ala Leu
65                  70                  75                  80

Ala Leu Leu Arg Lys Pro Asp Glu Phe Leu Ala Glu Gln Leu His Ala
                85                  90                  95

Ala Met Lys Gly Leu Gly Thr Asp Glu Asn Ala Leu Ile Asp Ile Leu
            100                 105                 110

Cys Thr Gln Ser Asn Ala Gln Ile His Ala Ile Lys Ala Ala Phe Lys
        115                 120                 125

Leu Leu Tyr Lys Glu Asp Leu Glu Lys Glu Ile Ile Ser Glu Thr Ser
    130                 135                 140

Gly Asn Phe Gln Arg Leu Leu Val Ser Met Leu Gln Gly Gly Arg Lys
145                 150                 155                 160

Glu Asp Glu Pro Val Asn Ala Ala His Ala Ala Glu Asp Ala Ala Ala
                165                 170                 175

Ile Tyr Gln Ala Gly Glu Gly Gln Ile Gly Thr Asp Glu Ser Arg Phe
            180                 185                 190

Asn Ala Val Leu Ala Thr Arg Ser Tyr Pro Gln Leu His Gln Ile Phe
        195                 200                 205

His Glu Tyr Ser Lys Ile Ser Asn Lys Thr Ile Leu Gln Ala Ile Glu
    210                 215                 220

Asn Glu Phe Ser Gly Asp Ile Lys Asn Gly Leu Leu Ala Ile Val Lys
225                 230                 235                 240

Ser Val Glu Asn Arg Phe Ala Tyr Phe Ala Glu Arg Leu His His Ala
                245                 250                 255

Met Lys Gly Leu Gly Thr Ser Asp Lys Thr Leu Ile Arg Ile Leu Val
            260                 265                 270

Ser Arg Ser Glu Ile Asp Leu Ala Asn Ile Lys Glu Thr Phe Gln Ala
        275                 280                 285

Met Tyr Gly Lys Ser Leu Tyr Glu Phe Ile Ala Asp Cys Ser Gly
    290                 295                 300

Asp Tyr Lys Asp Leu Leu Leu Gln Ile Thr Gly His
305                 310                 315
```